United States Patent [19]

Larrick et al.

[11] Patent Number: 4,677,070

[45] Date of Patent: Jun. 30, 1987

[54] PSEUDOMONAS AERUGINOSA EXOTOXIN A ANTIBODIES, THEIR PREPARATION AND USE

[75] Inventors: James W. Larrick, Woodside, Calif.; Andrew A. Raubitschek, Bethesda, Md.

[73] Assignee: Cetus Corporation, Emeryville, Calif.

[21] Appl. No.: 727,514

[22] Filed: Apr. 26, 1985

[51] Int. Cl.⁴ .................. C12N 5/00; C07K 15/04
[52] U.S. Cl. ..................... 435/240; 530/387; 435/68; 435/70; 435/172.2; 435/241; 424/85; 424/87; 935/100; 935/104; 935/107; 935/108; 935/110
[58] Field of Search ........... 435/68, 172.2, 240, 435/70, 241, 948; 424/85, 177, 87; 260/112 R; 935/95, 96, 99, 100, 102–104, 106, 107, 108, 110; 530/387, 388

[56] References Cited

U.S. PATENT DOCUMENTS

| 4,434,230 | 2/1984 | Ritts, Jr. | 435/240 |
| 4,443,549 | 4/1984 | Sadowski | 436/548 |
| 4,451,570 | 5/1984 | Royston et al. | 435/240 |
| 4,455,296 | 6/1984 | Hansen et al. | 424/87 |
| 4,464,465 | 8/1984 | Lostrom | 435/68 |
| 4,529,694 | 7/1985 | Lazarus et al. | 435/68 |

FOREIGN PATENT DOCUMENTS

| 0044722 | 1/1982 | European Pat. Off. |
| 0057107 | 8/1982 | European Pat. Off. |
| 0062409 | 10/1982 | European Pat. Off. |
| 0101039 | 2/1984 | European Pat. Off. |
| 0105804 | 4/1984 | European Pat. Off. |
| 0107528 | 5/1984 | European Pat. Off. |
| 0118893 | 9/1984 | European Pat. Off. |
| 0124301 | 11/1984 | European Pat. Off. |
| 0131878 | 1/1985 | European Pat. Off. |
| WO85/01659 | 4/1985 | PCT Int'l Appl. |
| 2086937 | 5/1982 | United Kingdom |
| 2113715 | 8/1983 | United Kingdom |

OTHER PUBLICATIONS

Olsson, L. et al., Proc. Natl. Acad. Sci., USA, 77(9): 5429–5431 (9–1980).
Cote, R. J. et al., Proc. Natl. Acad. Sci., USA 80: 2026–2030 (4–1983).
Teng, N. N. H. et al., Proc. Natl. Acad. Sci., USA, 80: 7308–7312 (12–1983).
*Human Hybridomas and Monoclonal Antibodies*, Engleman E., et al. (eds.)—Plenum Publishing Corp., 1985, pp. 149–165.
Fisher, M. W. (1977) J. Infect. Dis. 136, 5181–5185.
Apicella, M. A. et al., *Biological Abstracts*, vol. 73, 1982, ref. 83064, Infect. Immun. 34 (3), pp. 751–756 (1981).
Morse, S. A. et al., *Biological Abstracts*, vol. 74, 1982, ref. 61778 J. Infect. Dis. 145 (2) 206–216, 1982.
Hancock, R. E. W. et al., *Biological Abstracts*, vol. 75, 1983, ref. 10652 Infect. Immun. 37 (1):166–171, 1982.
Cross et al., J. Inf. Dis., 142, 538 (1980).
Pavlovskis et al., Inf. Immun., 18, 596–602 (1977).
Pollack, Rev. Inf. Dis., 5, 979–984 (1983).
Pollack, J. Inf. Dis., 147, 1090 (1983).
Cryz et al., Inf. and Imm., 40, 659–664 (1983).
Galloway et al., Inf. and Imm., 44, 262–267 (1984).
Foung et al., J. Immun. Meth., 70, 83–90 (1984).
D. Buck et al., Chapter 11 of *Monoclonal Antibodies and Functional Cell Lines*, ed. R. Kennett et al., Plenum Pub. Corp., 1984.
Mutharia et al., Inf. and Imm., 45, 631–636 (1984).

*Primary Examiner*—Margaret Moskowitz
*Attorney, Agent, or Firm*—Elliott L. Fineman; Janet E. Hasak; Albert P. Halluin

[57] ABSTRACT

Anti-Pseudomonas antibodies which bind to exotoxin A from *P. aeruginosa* are prepared from hybrid cell lines. The antibodies may be of any isotype. These antibodies may be used to treat infections caused by *P. aeruginosa*.

3 Claims, No Drawings

PSEUDOMONAS AERUGINOSA EXOTOXIN A ANTIBODIES, THEIR PREPARATION AND USE

BACKGROUND OF THE INVENTION

This invention relates to the production of antibodies directed against exotoxin A from *Pseudomonas aeruginosa*.

*Pseudomonas aeruginosa* is a highly virulent pathogen which infects patients receiving immunosuppressive therapy or suffering from severe thermal burns or other serious injuries, cystic fibrosis, or neoplastic diseases. Mortality from *P. aeruginosa* has been reduced as the result of such therapeutic agents as mafenide acetate and silver salts which inhibit bacterial colonization of the burn wound surface, potent antibiotics for treating bacteremia, and barrier isolation to minimize contact of the patient with hospital flora. Such agents, however, have only proved partially successful in controlling the morbidity and mortality associated with Pseudomonas infections.

Recently, researchers have found that specific antibodies constitute a critical immunologic defense mechanism against Pseudomonas disease; therefore, vaccines have been administered to patients in attempts to increase antibody titers in the patients. No non-toxic vaccines have been found to date which are particularly effective against the pathogen.

It is not yet clear what components of *P. aeruginosa* are responsible for its virulence. Many different types of infections are recognized, from acute localized eye infections and chronic lung infections to generalized systemic infections and septicemia. One of the most extensively studied components of *P. aeruginosa* is exotoxin A. (Iglewski et al., *Methods Enzymol.*, 60, 780–793 (1979)). Exotoxin A is on a weight basis the most potent extracellular product of *P. aeruginosa* and is produced by about 90% of clinical isolates regardless of Fisher-Devlin-Gnabasik immunotype. The mechanism of action of exotoxin A is similar to that of diphtheria toxin in that exotoxin A is synthesized as a proenzyne which catalyzes the transfer of the ADP ribose moiety from NAD into covalent linkage with elongation factor 2, thereby potentially inhibiting mammalian protein synthesis.

Antibody to endotoxin A has been found in normal human adults and was studies by Cross et al.,-*J. Inf. Dis.*, 142, 538 (1980) and by Pavlovskis et a., *Inf. Immun.*, 18, 596–602 (1977). See also Pollack, *Rev. Inf. Dis.*, 5, 979–984 (1983). Pollack, *J. Inf. Dis.* 147, 1090 (1983) studied the immunologic reactivity and opsonic and protective activity against *Pseudomonas aeruginosa* of twenty-seven lots of human immune globulin from seven producers. All contained hemagglutinating antibodies to exotoxin A.

Cryz et al., *Inf. and Imm.*, 40, 659–664 (1983) indicate that immunoglobulin G (IgG) fractions directed against exotoxin A are protective in experimentally infected animals. Hancock et al., *Inf. and Imm.*, 37, 166–171 (1982) describe preparation of mouse monoclonal antibodies against *P. aeruginosa* outer membrane antigens. Galloway et al., *Inf. and Imm.*, 44, 262–267 (1984) described mouse monoclonal antibodies specific to extoxin A. The literature reports the preparation of human monoclonal antibodies directed against various antigens. EP No. 81303286.9 published Jan. 27, 1982 is directed to human monoclonal antibodies and suggests making antibodies to "pathogen surface antigens" and "toxins". In addition, Foung et al., *J. Immun. Meth.*, 70, 83–90 (1984) discloses human monoclonal antibodies production from an EBV-transformed B cell line by fusion to a human-mouse hybridoma. Several fushion partners are described by D. Buck et al., Chapter 11 of *Monoclonal Antibodies and Functional Cell Lines*, ed. by R. Kennett et al., Plenum Publishing Corp., 1984. Mutharia et al., *Inf. and Imm.*, 45, 631–636 (1984) describe monoclonal antibodies specific for *E. coli* J5 LPS. Europ. Pat. Publications 107,528 and 105,804 describe cell lines capable of producing human monoclonal antibodies against a bacterial toxin. In addition, GB Nos. 2,086,937; 2,113,715; EP Nos. 57,107; 62,409; 118,893; 124,301 and 131,878 all relate to manufacture of human monoclonal antibodies from hybrid cells.

There is a need to develop monoclonal antibodies for passive immunotherapy of patients infected with *P. aeruginosa*.

SUMMARY OF THE INVENTION

Accordingly, the present invention provides an antibody which binds to exotoxin A of *Pseudomonas aeruginosa* and is selected from those antibodies whose population is substantially homogeneous, i.e., the antibody is monoclonal.

Another aspect of the invention herein is a stable, permanent cell line which produces such antibody and progeny of the cell line.

In addition, the invention relates to compositions for treating infections caused by *Pseudomonas aeruginosa* comprising a therapeutically effective amount of such antibody in association with a pharmaceutically acceptable parenteral vehicle. In one embodiment the infection is chronic endobronchitis endemic in cystic fibrosis patients.

In a further aspect, the invention relates to a method for treating a mammalian patient for infections caused by *P. aeruginosa* comprising administering an effective amount of such antibody to the patient parenterally.

In a still further aspect the invention relates to a stable, permanent cell line identified as D253-15-6 (CTCC #0087) and progeny thereof.

The antibodies herein may be successfully utilized for passive immumotherapy against, or prophylaxis of, Pseudomonas infections.

DESCRIPTION OF THE PREFERRED EMBODIMENTS

As used herein the term "cell line" refers to individual cells, harvested cells, and cultures containing cells so long as they are derived from cells of the cell line referred to.

As used herein with respect to hybrid cell lines, the term "progeny" is intended to include all derivatives, issue, and offspring of the cell lines regardless of generation of karyotypic identity.

As used herein with respect to a given antibody, the term "functional equivalent" means an antibody that recognizes the same determinant as and crossblocks the antibody referred to. It is intended to include antibodies of the same or different immunoglobin class and antigen binding fragments (e.g., Fab. F(ab')$_2$, Fv) of the antibody.

As used herein with respect to administering antibody to patients, the term "treat" and conjugates thereof refers to therapy and/or prophylaxis.

As used herein the term "monoclonal antibody" refers to an antibody selected from antibodies whose population is substantially homogeneous, i.e., the individuals of the antibody population are identical except for naturally occurring mutations.

As used herein with respect to characterizing the claimed hybrid cell lines, the terms "permanent" and "stable" mean that the lines remain viable over a prolonged period of time, typically at least about six months, and maintain the ability to produce the specified monoclonal antibody through at least about 50 passages.

As used herein the term "serotype" refers to one of the seven Fisher-Devlin-Gnabasik immunotypes of *P. aeruginosa* described by Fisher et al., *J. Bacteriol.*, 98, 833–836 (1969).

The antibodies herein against exotoxin A are monoclonal. Also, the antibodies herein may be any isotype, preferably IgM or IgG. They are made by fusion involving cells of diverse mammalian origin. Human embodiments have been made. The human embodiments may be the products of triomas synthesized by somatic cell hybridization using a mouse×human parent hybrid cell line and a human cell line producing sufficiently high levels of anti-exotoxin A antibodies. The latter cell line may be from, e.g., peripheral blood lymphocytes (PBL) and may be transformed with Epstein-Barr virus (EBV) as described, for example, by Foung, et al., *J. Immunol. Methods*, 70, 83–90 (1984). The latter cell line may be obtained from non-immunized volunteers screened for or known to contain high serum anti-exotoxin A *P. aeruginosa* titers of IgM, IgG and/or IgA.

When transformation is employed, the most successful approaches have been either to pre-select the population of B cells to be transformed or to post-select the antigen-specific transformed populations by panning or rosetting techniques, as described by Kozbar et al., *Scan. J. Immunol.*, 10, 187–194 (1979) and Steinitz et al., *J. Clin. Lab. Immun.*, 2, 1–7 (1979). Recently EBV transformation has been combined with cell fusion to generate human monoclonal antibodies (see, e.g., Foung, et al., *J. Immun. Meth.*, 70, 83–90 (1984)), due to instability of immunoglobulin secretion by the EBV transformed lines, increased immunoglobulin secretion by hybridomas when compared to EBV lymphoblastoid cell lines, and higher frequencies of rescue of the antigen-specific populations.

EBV most frequently infects and transforms IgM-bearing B cells, but B cells secreting other classes of Ig can also be made into long-term lines using the EBV fusion technique, as described by Brown and Miller, *J. Immunol.*, 128, 24–29 (1982).

One strategy for preparing and identifying hybridomas which produce human antibodies of the invention follows. Peripheral blood cells are obtained from cystic fibrosis patients chronically colonized with *P. aeruginosa* and known to have substantial titers of antiexotoxin A *P. aeruginosa* antibodies. Lymphocytes are transformed with Epstein-Barr virus and the lymphoblastoid cell lines are screened by ELISA using exotoxin A from *P. aeruginosa*. The positive cell lines are then subcultured twice, the subcultures are screened, and the positive subcultures are fused to a fusion partner consisting of a mouse×human B cell hybrid resistant to ouabain and 6-thioguanine by the technique described by Truitt et al. in *Monoclonal Antibodies and Functional Cell Lines* (ed. by R. H. Kennett et al.), Plenum, New York: 1984. In the selection medium ouabain is used to kill unfused EBV transformants, and hypoxanthine and azaserine are used to kill unfused mouse×human fusion partner. Supernatants from the selected growing hybrid cells are screened by ELISA against exotoxin A bacteria. Hybrids which are positive are cloned by limiting dilution. Cloned wells showing immunoblot binding to exotoxin A are used to produce monoclonal antibodies.

The antigen-binding ability of the antibodies herein is evaluated by immunoblots and ELISAs. Those antibodies which have the ability to block the adverse biological effects of *P. aeruginosa* exotoxin A in mammals regardless of the mechanism involved are preferred. Examples of such useful properties include the ability to neutralize the toxic effects of exotoxin A or to increase the rate of catabolism and/or clearance of exotoxin A, etc.

The cell lines which produce the antibodies of this invention may be grown in suitable culture media such as Iscove's media or RPMI-1640 medium from Gibco, Grand Island, NY, or in vivo in immunodeficient laboratory animals. If desired, the antibody may be separated from the culture medium or body fluid, as the case may be, by conventional techniques such as ammonium sulfate precipitation, hydroxylapatite chromatograph, ion exchange chromatography, affinity chromatography, electrophoresis, microfiltration, and ultracentrifugation.

The antibodies of this invention may be used passively to immunize individuals who suffer from *P. aeruginosa* septicemia or are at risk with respect to *P. aeruginosa* infection. Patients at risk include those receiving immunosuppressive therapy and those suffering from severe thermal burns or other serious injuries, cystic fibrosis and cancer. One possible treatment is from chronic endobronchitis infection endemic in cystic fibrosis patients.

The antibodies may be administered to the patient by any suitable technique, including subcutaneous and parenteral administration, preferably parenteral. Examples of parenteral administrtion include intravenous, intraarterial, intramuscular and intraperitonael, preferably intravenous. The dose and dosage regimen will depend mainly upon whether the antibody/antibodies is/are being administered for therapeutic or prophylactic purposes, the patient, and the patient's history. The total pharmaceutically effective amount of an antibody administered per dose will typically be in the range of about 0.2 to 20 mg/kg of patient body weight.

For parenteral administration the antibody/antibodies will generally be formulated in a unit dosage injectable form (solution, suspension, emulsion) in association with a pharmaceutically acceptable parenteral vehicle. Such vehicles are inherently nontoxic and non-therapeutic. Examples of such vehicles include water, saline, Ringer's solution, dextrose solution, and 5% human serum albumin. Nonaqueous vehicles such as fixed oils and ethyl oleate may also be used. Liposomes may be used as carriers. The vehicle may contain minor amounts of additives such as substances which enhance isotonicity and chemical stability, e.g., buffers and preservatives. The antibody will typically be formulated in such vehicles at a concentration of about 0.1 mg/ml to 100 mg/ml.

The various aspects of the invention are further described by the following examples, which are not intended to limit the invention in any manner. In these examples all percentages for solids are by weight and all percentages for liquids and gases are by volume unless otherwise noted, and all temperatures are given in degrees Celsius.

EXAMPLE I

A. Fusion Partners

I. Human B Lymphocytes

Volunteer patients having cystic fibrosis and screened as having serum anti-exotoxin A titers (IgM, IgG and/or IgA) all greater than 1:2000 were selected. Fifty ml of venous blood was drawn on day 1 and treated in sodium citrate. The blood was centrifuged and the buffy coat was harvested and then gradient centrifuged using Ficoll/Hypaque to separate lymphocytes. T cells were removed by AETSRBC rosetting to yield $5.2 \times 10^6$ cells as described by Madsen et al., *J. Immunol. Methods,* 27: 61–74 (1979). The remaining B cell-enriched lymphocyte population was transformed with Epstein-Barr virus as described by Foung et al., supra, except that cells were cultured at $10^3$–$10^4$ cells per well in five 96-well microtiter plates. The wells were screened by a specific ELISA test using purified exotoxin A as described further below.

At day 20, 22 out of 480 wells were highly positive by exotoxin A ELISA screen. Six of these wells were subcultured at 500 cells/well on day 24. At day 37 all positive wells were further subcultured. At day 48 two of the most positive wells were selected for expansion and antibody production and were cloned by limiting dilution using 0.3 cells per well in 96-well U-bottom plates (Costar) in Iscove's DME medium with 20% FBS. These two subclones were then fused to F3B6 as described below.

II. F3B6 (Mouse × Human Line)

A mouse-human heterohybrid fusion partner designated F3B6 (adapted to 99% serum-free medium and deposited with the ATCC under ATCC Accession No. HB 8785 on Apr. 18, 1985) was constructed by fusing peripheral blook lymphocyte (PBL) B cells obtained from a blood bank with the murine plasmacytoma cell line NS-1 obtained from ATCC under ATCC No. TIB18(P3/NS1/1-AG4-1). The PBL cells from random buffy coat were transferred to a 50 ml centrifuge tube and diluted with 30 ml Hanks' balanced salt solution ($Ca^{2+}$-free/$Mg^{2+}$-free) (HBSS−/−). Then 10 ml Ficoll-Hypaque was added and the mixture centrifuged at 1500 rpm for 15 minutes at room temperature. The interface was removed and the mixture was washed with HBSS−/− and resuspended in HBSS−/−. The cells were counted.

The NS-1 cells were grown in 4×T75 flasks and harvested, washed with HBSS−/− and resuspended in HBSS−/−. The cells were counted.

Approximately $5 \times 10^7$ B-cells and $2.5 \times 10^7$ NS-1 cells (2:1 ratio) were added to each of 5–50 ml centrifuge tubes for fusion. The mixture was centrifuged at 1200 rpm for eight minutes at room temperature to form a tight pellet. All of the supernatant was removed and the tube was kept at 37° C. for further manipulations. A total of 1 ml of warm 50% polyethyleneglycol of molecular weight 1540 (PEG 1540) (BDH Chemicals, Poole, England) was added over a one minute period using a 1 ml pipette. The cell pellet was gently stirred with the tip of the pipette as the PEG was being added. Then 1 ml of HBSS−/− was added at 37° C. over a one-minute period to dilute gradually the PEG. The cells were washed twice with HBSS−/− and resuspended in Iscove's medium in several T150 flasks.

On day 2 the cells were washed in HBSS−/− in 50 ml centrifuge tubes. A total of 10 ml of Ficoll-Hypaque was added to the tubes. The tubes were centrifuged at 1500 rpm for 15 minutes at room temperature and the live cells at the interface were removed. The pellet was washed twice with RPMI-1640 (Gibco) and resuspended in an enriched hypoxanthine/azaserine selection medium (EHA) consisting of 100 μM hypoxanthine (Sigma), 5 μg/ml azaserine (Sigma) and Iscove's medium (Gibco), 10% NCTC (M. A. Biologicals), 20% heat-inactivated-FBS. The density was adjusted to $2.5 \times 10^4$ cells/ml medium.

At day 5 the suspensions were washed twice with HBSS−/− and resuspended in 10 ml Iscove's medium. Live cells were separated by Ficoll-Hypaque density gradient centrifugation as described above. Cells were washed twice with RPMI-1640+20% FBS, and then plated out in 96-well plates at $10^6$ cells/ml. At days 7, 9 and 12 the EHA selection medium described above was added each time. At days 15 and 18 the plates were fed with EHMT medium containing hypoxanthine, methotrexate and thymidine. The supernatants were assayed for Ig secretion and Ig secreting hybrid cell lines were cloned by limiting dilution in U bottom 96 well plates.

Well B6 was selected for 6-thioguanine selection. Several roller bottles of F3B6 were grown up. A total of 10 μg/ml of 6-thioguanine was added to the roller bottles. Dead cells were removed by Ficoll-Hypaque density gradient centrifugation on days 2, 5 and 7. A 6-thioguanine resistant clone was grown up. Test fusions were performed, and the cell line was tested for ouabain resistance.

The resultant cell line was adapted to growth and maintenance in 99% serum-free medium and 1% FBS for more reproducible manufacturing by the following multi-step process:

1. Two days prior to subculturing, the cells were fed with a mixture of the Iscove's DME in which they were growing, 50% of the amount of FBS in the medium in which they were growing, and 50% by weight of serum-free medium HL-1 supplied by Ventrex, Inc.
2. Two days later, or when the hybridoma cells reached densities of $8 \times 10^5$ to $1 \times 10^6$ cells/ml, the cells were subcultured and planted with 50% of Iscove's DME medium and 50% of the serum-free medium. The cells were removed from the latter medium by centrifugation at 200×g for five minutes. The Iscove's DME medium was mixed with 50% of the serum-free medium to form a 50:50 mixture, in which the cell pellet was suspended and then counted. An appropriate amount of cell suspension was planted in the vessel with 50% Iscove's DME and 50% serum-free medium. The planted cell densities preferably do not fall below $5 \times 10^4$ cells/ml and not exceed $1 \times 10^5$ cells/ml.
3. After two to three days post-planting, or when the cell density reached $8 \times 10^5$ to $1 \times 10^6$ cells/ml, the cells were refed with 50% Iscove's DME and 50% serum-free medium.
4. Step 3 was repeated for another passage.
5. After two to three days in culture or when the cell density reached $8 \times 10^5$ to $1 \times 10^6$ cells/ml and viability was about 85%, the cells were cultured on serum-free medium only. When the cells were planted in the serum-free medium for the first time the cell densities were between $1 \times 10^5$ to $8-9 \times 10^5$ cells/ml. The final medium was HL-1 with 1% FBS.

B. Fusion Protocol

The fusion mixture contained polyethylene glycol (PEG) 4000, 40% (w/v); dimethylsulfoxide (DMSO), 10% (v/v) and 5 μg/ml poly-1-arginine in Hanks' balanced salt solution (HBSS)−/+ ($Ca^{2+}$-free, 2 mM $MgSO_4$), Forty g of PEG 4000 was combined with 10 ml of DMSO and 50 ml of HBSS−/+. The mixture was autoclaved for 25 minutes. Before use, the pH of the fusion mixture was adjusted to between 7.5 and 8.5 with sterile 0.1N NaOH.

Plates (6-well cluster, 35 mm well diameter) were prepared as follows: 2 ml of HBSS−/+ and 50 μl of a filter sterilized, 20–100 μg/ml, peanut agglutinin (PNA, Sigma) were added to each well. Plates were incubated at 37° C. for at least one hour prior to use. PNA stock was stored frozen, and a freshly thawed aliquot was used to coat fusion cells. Smaller sized wells were used if cell numbers were limited.

Parent cells in Ficoll-Hypaque were washed twice in HBSS−/+ at room temperature and subsequently resuspended and combined at a ratio of 5:1 to 1:1 highest titer lymphocyte:F3b6 in HBSS−/+ warmed to 37° C. Two ml of the combined cell suspension ($3 \times 10^7$ cells/well) was added to each pretreated well containing 1 μg/ml PNA coating solution. The wells were incubated at 37° C. for one minute. Plates were spun onto bottom of the plate at $400-500 \times g$, room temperature, for five minutes to form a monolayer of cells. Supernatant was then aspirated off the plates, leaving behind adherent coating of cells.

Two ml of PEG fusion mixture described above and warmed to 37° C. was carefully added down the side of the fusion well. After one minute, the PEG solution was diluted with a fusion dilution mixture (FDM) of 5% DMSO (Sigma) HBSS−/+ (warmed to 37° C. and filter sterilized) at a rate of 2 ml/min (0.5 ml every 15 sec) for the next two-three min (4–6 ml). For the next two minutes the FDM was added at a rate of 4 ml/min with mixing. FDM was always added down the side of the well, so as not to disturb the monolayer, and the plates were swirled constantly to ensure optimal mixing.

At the end of the two minutes the wells were aspirated to remove diluted PEG fusion mixture. The remaining film of PEG mixture was diluted at a rate of 2 ml/min for one-two min with warm FDM. Again the plate was constantly swirled. Over a period of 0.25–2 minutes with swirling, 5 ml of HBSS−/+ warmed to 37° C. was added to the fusion well at a rate of 1 ml/15 sec. The well was then filled up with HBSS−/+ and all supernatant was aspirated from the monolayer. Finally, each fusion well was washed once or twice with about 5–10 ml of warm HBSS−/+, aspirated and washed again with about 5 ml of HBSS−/+ and aspirated. Five ml of warm Iscove's complete medium and 15–20% FBS, were added to each well, and the plates were incubated at 37° C. for 24 hours. The day following fusion the cells were resuspended at a density of $10^5$ cells/ml in HA medium containing azaserine (2–5 μg/ml), hypoxanthine (100 μM), in Iscove's DME medium with 15% FBS, and plated at 0.1 ml/well in 96-well plates. Cultures were subsequently fed every three days. Growing hybrids were visible within 14 to 21 days.

C. ELISAs

I. Exotoxin A

A total of 50 μl of purified exotoxin A (10 μg/ml) ($M_R$-66 Kd obtained from Dr. Iglewski, Univ. of Oregon Health Center and S. Leppla, Fort Detrick, Md.) in 50 mM $NaHCO_3$ buffer at pH 9.5 was coated onto flat-bottom microtiter plates (Dynatech). After overnight incubation at room temperature the plates were washed with phosphate buffered saline containing 0.1 g/liter $MgSO_4$ and 0.1 g/liter $CaCl_2$ (PBS++), and 0.05% Tween 20 surfactant (Sigma), and then 100 μl of 1% bovine serum albumin (BSA) and 0.05% Tween-20 in PBS. Then 100 μl of the supernatant was added to each plate and the plate was incubated at 4° C. for 30 minutes. The wells were then washed as described above and the plate bottom was optionally blotted with soft tissue. Fifty-100 μl of horseradish peroxidase-conjugated goat anti-human Ig developing reagent (Zymed) was then added to each well. The wells were incubated at 4° C. for 30 minutes and then washed again with PBS++. Two-hundred μl of ABTS substrate was then added to each well, the substrate consisting of 55 mg/ml of ABTS aqueous stock solution diluted 1:1000 with 0.1M sodium citrate buffer at pH 4.5 to which 1:1000 of 30% $H_2O_2$ was added immediately before use. Each well was incubated for 30 minutes at 37° C. in the dark. The contents of the wells were transferred to a transparent plate and were read with an ELISA reader at 405 nm. Readings were reported on a sale of 1 to 10 with 1=0.0 OD, 10=2.0 OD.

II. IgM

Immulon II flat-bottom microtiter plates were coated at 100 μl/well with goat anti-human IgM (Tago) diluted 1:100 in 50 mM bicarbonate buffer (pH 9.6). After 90 minutes at 37° C., plates were washed with PBS++, 0.05% Tween 20, and preferably 0.01% thimerosal up to five times by immersion or with automated plate washer. Then 100 of PBS++, 1% BSA, 0.05% Tween 20, 0.1% thimerosal was preferably added to each well. A total of 100 μl of test supernatant was added to first wells and preferably duplicate two-fold dilutions were made. One well was preferably left as control. The plates were incubated for 30 minutes at 22° C. and then washed up to five times as described above. Then, a total of 50–100 μl of peroxidase-conjugated goat anti-human IgM antibody (Tago) diluted in PBS++, BSA, Tween 20 thimerosal was added and the mixture incubated for 30 minutes at room temperature or 40° C. and washed up to five times. Then a total of 200 μl of the ABTS peroxidase substrate described for the bacterial ELSIA was added to each well. The mixture was incubated for 30 minutes at 37° C. in the dark and read on an ELISA plate reader ($OD_{405}$) using as IgM standard pooled human myeloma (Cappell) previously standardized versus a Tago Standard.

D. Hybrid Screening (B Lymphocyte×F3B6)

Culture supernatants were assayed by exotoxin A ELISA as described above. Both parent EBV cell lines selected for antibody production yielded positive anti-exotoxin A secreting progeny. Most of the clones of one line made appreciable amounts of specific antibody. For selecting of high producer hybrids, an antigen-specific plaque technique and a non-specific Ig reverse-plaque technique were both useful. For reverse-plaque, Protein A-coated sheep erythrocytes (1.0%) were added to the upper layer of soft agar according to the method of Gronowicz et al., PNAS (USA), 6, 588–590 (1976).

Using the IgM ELISA described above all of these antibodies were found to be of the IgM class. Two of the IgM antibodies generated were used to immunoblot exotoxin A by the technique essentially described by Wang and Larrick, "Immunoblotting", in *Human Hybridomas and Monoclonal Antibodies,* Engleman et al., Plenum: New York, 1985. They recognized the single chain 66 Mr exotoxin A protein. A mixture of these antibodies gave a three-fold increase in the $ID_{50}$ of exotoxin A activity in a fibroblast proliferation assay.

The two monoclonal antibodies produced from the above hybrids were isolated and found to be IgMs. A sample of the mousehuman hybridoma cell line which produces one type of antibodies were is the better of the two, was adapted to serum-free medium HL-1 by the same procedure was described for F3B6 except that the medium is 100% serum free. This hybridoma was deposited at the Cetus Tissue Culture Collection of the assignee (CTCC) and at the American Type Culture Collection (ATCC), 12301 Parklawn Drive, Rockville, Md., USA. Deposit dates and accession numbers are given below for this cell line and for the mouse×human fusion partner (adapted to 99% serum-free medium) used to prepare it (F3B6).

| Cell Line | Deposit Date | CTCC # | Accession No. |
|---|---|---|---|
| D253-15-6 | 25 April 1985 | 0087 | HB 8789 |
| F3B6 | 18 April 1985 | | HB 8785 |

The deposits above were made pursuant to a contract between the ATCC and the assignee of this patent application, Cetus Corporation. The contract with ATCC provides for permanent availability of the progeny of these cell lines to the public on the issuance of the U.S. patent describing and identifying the deposit or the publications or upon the laying open to the public of any U.S. or foreign patent application, whichever comes first, and for availability of the progeny of these cell lines to one determined by the U.S. Commissioner of Patents and Trademarks to be entitled thereto according to 35 USC §122 and the Commissioner's rules pursuant thereto (including 37 CFR §1.14 with particular reference to 886 OG 638). The assignee of the present application has agreed that if the cell lines on deposit should die or be lost or destroyed when cultivated under suitable conditions, it will be promptly replaced on notification with a viable culture of the same cell lines.

Modifications of the above-described modes for carrying out the invention that are obvious to those of skill in the fields of hybridoma technology, immunology, bacterial infections, and related fields, are intended to be within the scope of the following claims.

What is claimed is:

1. Cell line HB 8789.

2. An anti-pseudomonas monoclonal antibody produced by cell line HB 8789 which binds to exotoxin A of Pseudomonas.

3. Anti-pseudomonas exotoxin A monoclonal antibodies, produced by cell line HB 8789 and the progeny thereof.

* * * * *